(12) United States Patent     (10) Patent No.:   US 12,674,156 B2

Chen et al.     (45) Date of Patent:    Jul. 7, 2026

(54) NANOZYME MATERIAL AND PREPARATION METHOD THEREOF, AND DETECTION METHOD OF LEAD (II) ION

(71) Applicant: YUNNAN TOBACCO QUALITY SUPERVISION AND TESTING STATION, Kunming (CN)

(72) Inventors: Dan Chen, Kunming (CN); Yaling Yang, Kunming (CN); Huimin Deng, Kunming (CN); Chunqiong Wang, Kunming (CN); Li Chen, Kunming (CN); Yifan Cui, Kunming (CN); Ke Zhang, Kunming (CN); Shichun Qin, Kunming (CN); Yuemao Wang, Kunming (CN); Xiaodong Hu, Kunming (CN); Xiaodong Yin, Kunming (CN); Yunfang Zhao, Kunming (CN); Lijuan Peng, Kunming (CN); Jie Long, Kunming (CN); Jieyun Cai, Kunming (CN); Haowei Sun, Kunming (CN); Dan Li, Kunming (CN)

(73) Assignee: YUNNAN TOBACCO QUALITY SUPERVISION AND TESTING STATION, Kunming (CN)

( * ) Notice: Subject to any disclaimer, the term of this patent is extended or adjusted under 35 U.S.C. 154(b) by 472 days.

(21) Appl. No.: 18/135,754

(22) Filed: Apr. 18, 2023

(65) Prior Publication Data

US 2024/0218348 A1     Jul. 4, 2024

(30) Foreign Application Priority Data

Dec. 29, 2022    (CN) .......................... 202211705187.6

(51) Int. Cl.

| | |
|---|---|
| *C12N 9/96* | (2006.01) |
| *B82Y 5/00* | (2011.01) |
| *C12Q 1/28* | (2006.01) |
| *G01N 21/78* | (2006.01) |
| *G01N 33/543* | (2006.01) |

(52) U.S. Cl.
CPC .................. *C12N 9/96* (2013.01); *B82Y 5/00* (2013.01); *C12Q 1/28* (2013.01); *G01N 21/78* (2013.01); *G01N 33/54346* (2013.01)

(58) Field of Classification Search
None
See application file for complete search history.

(56) References Cited

PUBLICATIONS

Lopez-Cantu et al., "Enzyme-mimicking capacities of carbon-dots nanozymes: Properties, catalytic mechanism, and applications—A review", vol. 194, pp. 676-687 (Year: 2022).*

Zheng-Jun Xie, et al., Colorimetric determination of Pb2+ ions based on surface leaching of Au@Pt nanoparticles as peroxidase mimic, Microchimica Acta, 2020, pp. 1-7, vol. 187, No. 255.

Kai Sun, et al., MnO2 nanozyme induced the chromogenic reactions of ABTS and TMB to visual detection of Fe2+ and Pb2+ ions in water, International Journal of Environmental Analytical Chemistry, 2019, pp. 1-14.

Li Xiao-Kun, et al., Gold Nanoparticle-based Colorimetric Assay for Determination of Lead(II) in Aqueous Media, Chemical Research in Chinese Universities, 2010, pp. 194-197, vol. 26, No. 2.

Guangda Xu, et al., Examples in the detection of heavy metal ions based on surface-enhanced Raman scattering spectroscopy, Nanophotonics, 2021, pp. 4419-4445, vol. 10, No. 18.

Charu Dwivedi, et al., Direct Visualization of Lead Corona and its Nanomolar Colorimetric Detection Using Anisotropic Gold Nanoparticles, ACS Applied Materials & Interfaces, 2015, pp. 5039-5044, vol. 7.

* cited by examiner

*Primary Examiner* — Anand U Desai

(74) *Attorney, Agent, or Firm* — OPENPTO US LLC; Yuhao Liang

(57)      ABSTRACT

A nanozyme material and a preparation method thereof are provided. In the preparation method, Prussian blue (PB) is used to regulate the peroxidase activity of Fe,NA/CDs, and then gold nanoparticles are synthesized with Fe,NA/CDs as a reducing agent and a stabilizing agent. The nanozyme material has both a peroxidase activity and a Raman enhancement effect, which can be used for nanozyme-based surface-enhanced Raman spectroscopy (SERS). An embodiment of the present disclosure also provides a method for rapidly detection of a $Pb^{2+}$ ion, which is based on a color change or an additional Raman SERS signal generation caused by nanozyme oxidation. Such sensing signals (colorimetric and SERS analysis) are derived from a catalytic oxidation reaction of ABTS or TMB, while the presence of $Pb^{2+}$ specifically inhibits the oxidation, such that the rapid detection of $Pb^{2+}$ can be achieved.

5 Claims, 3 Drawing Sheets

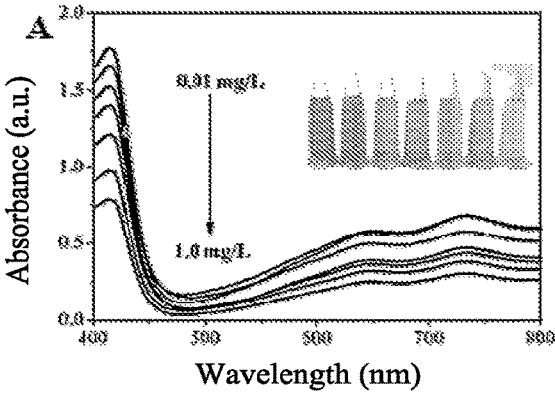
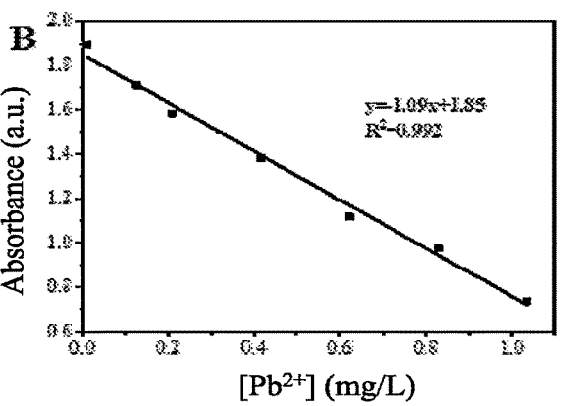
FIG. 3A                           FIG. 3B
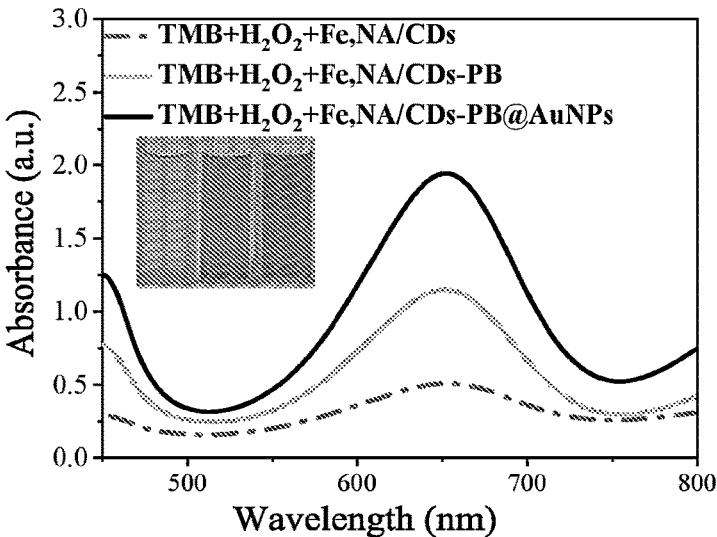
FIG. 4

NANOZYME MATERIAL AND PREPARATION METHOD THEREOF, AND DETECTION METHOD OF LEAD (II) ION

CROSS REFERENCE TO THE RELATED APPLICATIONS

This application is based upon and claims priority to Chinese Patent Application No. 202211705187.6, filed on Dec. 29, 2022, the entire contents of which are incorporated herein by reference.

TECHNICAL FIELD

The present disclosure relates to the technical field of ion detection, in particular to a nanozyme material and a preparation method thereof, and a detection method of a $Pb^{2+}$ ion.

BACKGROUND

Lead ions ($Pb^{2+}$) are non-degradable toxic metal ions. Lead ions are widely distributed in the environment due to industrial and mining activities, coal combustion, and the use of lead-containing paint/gasoline. The World Health Organization (WHO) recommends that a maximum residue limit (MRL) of $Pb^{2+}$ in drinking water is 10 μg/L and an MRL of $Pb^{2+}$ in food is 0.02 mg/kg to 0.5 mg/kg. In addition, metal preparations including lead or the like are pesticides with a severe impact on agricultural production safety, human and animal health, and environmental safety and have been listed as one of the banned pesticides inside and outside China. Therefore, the determination of $Pb^{2+}$ content is very important in the inspection of food safety. Currently, lead determination methods mainly include atomic absorption spectroscopy (AAS), atomic fluorescence spectrometry (AFS), inductively coupled plasma mass spectrometry (ICP-MS), an electrochemical method, and a colorimetric probe method. The colorimetric probe method has attracted much attention due to its advantages, such as simple and fast operations and complicated instruments are not needed. To achieve the ultra-sensitive determination of $Pb^{2+}$, signal amplification is often required in studies to achieve excellent sensitivity and low detection limits.

As a group of new enzyme mimics, nanozymes have many advantages that traditional enzyme mimics do not have, and investigation can be conducted and applications can be developed according to the characteristics of nanozymes, which makes nanozymes have promising application prospects. In recent years, nanozymes, including laccase mimicking enzymes, have been widely used in food analysis, biosensing, medical diagnosis, and industrial production. In surface-enhanced Raman spectroscopy (SERS), a Raman signal of a target substance is greatly enhanced with a precious metal material such as gold and silver to achieve the detection of a trace substance. SERS has advantages such as simple sample pretreatment, high detection speed, and low sample amount in addition to fingerprint spectral characteristics, and thus occupies a unique position in the field of food safety inspection. Recently, some nanomaterials have been prepared into SERS substrates with satisfactory oxidase-like activities that can be used to monitor a catalytic process of an oxidase-like reaction. However, these nanomaterials will be mostly dispersed into a solution with few SERS hotspots during detection, resulting in weak SERS enhancement of an adsorbed molecule and difficult recovery. Therefore, it is of great significance to develop a recyclable bifunctional nanostructure with SERS and enzyme-like activities.

SUMMARY

The first objective of the present disclosure is to provide a nanozyme material and a preparation method thereof. The nanozyme material is obtained through the assembly of iron-doped carbon dots and Prussian blue (PB) with gold nanoparticles. The nanozyme material has a novel structure, high activity, and high stability, and exhibits high application values in the detection of $Pb^{2+}$ ions.

A second objective of the present disclosure is to provide a method for rapidly detecting a $Pb^{2+}$ ion, where the nanozyme material is used to achieve the two different detection modes of colorimetric assay/SERS, and the results of the two detection modes are complementary and consistent, resulting in high detection sensitivity and reliability.

Embodiments of the present disclosure are implemented as follows:

A nanozyme material is provided, where the nanozyme material is Fe,NA/CDs-PB@AuNPs, and the nanozyme material includes iron-doped norepinephrine carbon dots Fe,NA/CDs, PB loaded on the Fe,NA/CDs, and AuNPs distributed on a surface of the Fe,NA/CDs.

A preparation method for the nanozyme material is provided, including:

mixing Fe,NA/CDs-PB, $H_2O_2$, sodium citrate, and $HAuCl_4$ to obtain a mixed solution, and subjecting the mixed solution to a reaction to obtain the Fe,NA/CDs-PB@AuNPs.

A use of the nanozyme material in the detection of a $Pb^{2+}$ ion is provided.

A method for detecting a $Pb^{2+}$ ion based on SERS is provided, including:

mixing the nanozyme material with a $Pb^{2+}$ ion solution, adding $H_2O_2$ and a 3,3',5,5'-tetramethylbenzidine (TMB) solution to allow a reaction, and subjecting a resulting reaction solution to Raman spectroscopy.

A method for detecting a $Pb^{2+}$ ion based on ultraviolet-visible (UV-vis) spectroscopy is provided, including:

mixing the nanozyme material with a $Pb^{2+}$ ion solution, adding $H_2O_2$ and a diammonium-2,2'-azino-bis (3-ethylbenzothiazoline-6-sulfonate (ABTS) solution to allow a reaction, and subjecting a resulting reaction solution to UV-vis spectroscopy.

The embodiments of the present disclosure have the following beneficial effects:

An embodiment of the present disclosure provides a nanozyme material and a preparation method thereof. In the preparation method, PB is used to regulate the peroxidase activity of Fe,NA/CDs, and then gold nanoparticles are synthesized with Fe,NA/CDs as a reducing agent and a stabilizing agent. The nanozyme material has both a peroxidase activity and a Raman enhancement effect and can be used for nanozyme-based SERS. An embodiment of the present disclosure also provides a method for rapidly detecting a $Pb^{2+}$ ion, which is based on a color change or an additional Raman SERS signal caused by nanozyme oxidation. Such a sensing signal (colorimetric and SERS analysis) is derived from a catalytic oxidation reaction of ABTS or TMB, and the presence of $Pb^{2+}$ specifically inhibits the oxidation, such that the rapid detection of $Pb^{2+}$ can be achieved. In addition, the results of colorimetric assay and SERS are complementary and consistent, which improves the accuracy and reliability of detection results.

BRIEF DESCRIPTION OF THE DRAWINGS

To describe the technical solutions in the examples of the present disclosure more clearly, the accompanying drawings required for describing the examples are briefly described below. It should be understood that the following accompanying drawings show merely some examples of the present disclosure, and thus should not be regarded as a limitation to the scope. An ordinary technician in similar field may still derive other related drawings from these accompanying drawings without creative efforts.

FIGS. 3A-3B show linear spectra and an equation for UV-vis spectroscopy-based detection of $Pb^{2+}$ provided in Example 3 of the present disclosure;

FIG. 4 shows spectra of TMB and $H_2O_2$ oxidized by Fe,NA/CDs, Fe,NA/CDs-PB, and Fe,NA/CDs-PB@AuNPs provided in Test Example 1 of the present disclosure;

DETAILED DESCRIPTION OF THE EMBODIMENTS

Figures 1A, 1B:
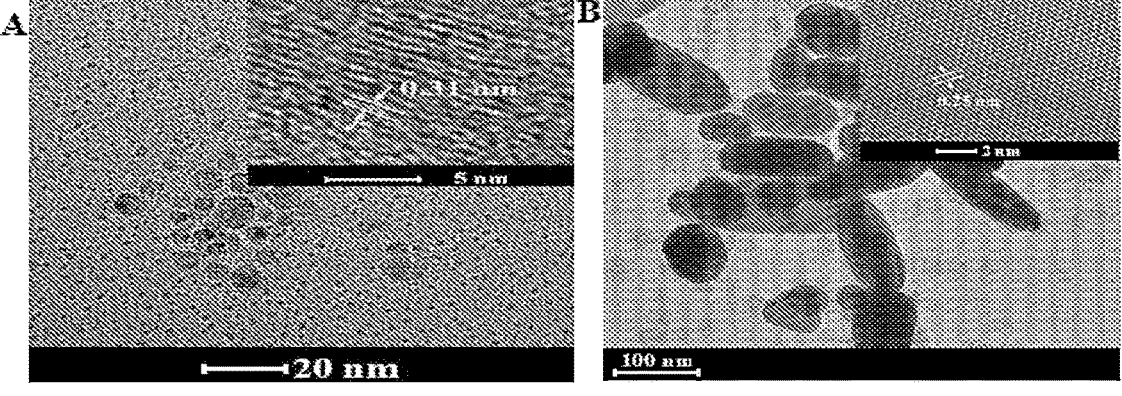
FIGS. 1A-1B show transmission electron microscopy (TEM) images of Fe,NA/CDs-PB and Fe,NA/CDs-PB@AuNPs provided in Example 1 of the present disclosure.

To make the objectives, technical solutions, and advantages of the examples of the present disclosure clearer, the technical solutions in the examples of the present disclosure will be described clearly and completely below. If no specific conditions are specified in the examples, the examples will be implemented under conventional conditions or the conditions recommended by the manufacturer. All of the used reagents or instruments which are not specified by manufacturers are conventional commercially-available products.

A nanozyme material and a preparation method and use thereof and a detection method of a $Pb^{2+}$ ion in the embodiments of the present disclosure are specifically described below.

An embodiment of the present disclosure provides a nanozyme material, where the nanozyme material is Fe,NA/CDs-PB@AuNPs, and the nanozyme material includes iron-doped norepinephrine carbon dots Fe,NA/CDs, PB loaded on the Fe,NA/CDs, and AuNPs distributed on a surface of the Fe,NA/CDs.

The nanozyme material is a gold nanoparticle synthesized as follows: PB is used to regulate a peroxidase activity of Fe,NA/CDs (iron-doped norepinephrine carbon dots), and then the gold nanoparticle is synthesized with the Fe,NA/CDs as a reducing agent and a stabilizing agent. The nanozyme material has both a peroxidase activity and a Raman enhancement effect and can be used for nanozyme-based SERS.

An embodiment of the present disclosure provides a preparation method for the nanozyme material, including:

mixing Fe,NA/CDs-PB, $H_2O_2$, sodium citrate, and $HAuCl_4$ to obtain a mixed solution, and subjecting the mixed solution to a reaction to obtain the Fe,NA/CDs-PB@AuNPs.

Fe, NA/CDs-PB, $H_2O_2$, and sodium citrate are in a mass ratio of 1:(0.02-0.2):(1-3); and a concentration of the $HAuCl_4$ in the mixed solution is 5 mg/mL to 20 mg/mL. The above ranges can ensure that the AuNPs (gold nanoparticles) have a prominent loading effect.

Further, Fe,NA/CDs-PB, $H_2O_2$, and sodium citrate are mixed in water, and based on a mass of Fe,NA/CDs-PB, 2 L to 4 L of water are added per g of Fe,NA/CDs-PB. $H_2O_2$ is preferably used in a solution with a concentration of 30 mmol/L to 70 mmol/L. The mixed solution can be stirred at room temperature for 5 min to 10 min to obtain the desired Fe,NA/CDs-PB@AuNPs.

Optionally, a preparation method of the Fe,NA/CDs-PB includes:

mixing a solution of PB in hydrochloric acid with Fe,NA/CDs to obtain Fe,NA/CDs-PB, where a mass ratio of Fe,NA/CDs to PB is 1:(20-60). The above range allows PB to have a prominent loading effect.

Further, the solution of PB in hydrochloric acid has a concentration of 0.05 mol/L to 0.3 mol/L, and based on a mass of PB, 0.1 L to 0.5 L of a hydrochloric acid solution is added per g of PB, which ensures the uniform dissolution of PB. The mixing of the solution of PB in hydrochloric acid with the Fe,NA/CDs can be achieved by stirring at room temperature for 40 min to 90 min.

Optionally, a preparation method of the Fe,NA/CDs includes:

mixing norepinephrine bitartrate, ethylenediamine (EDA), and iron chloride, and subjecting a resulting mixture to a reaction at 160° C. to 200° C., where the norepinephrine bitartrate, the EDA, and the iron chloride are in a mass ratio of 1:(0.2-0.5):(0.03-0.15). The preparation of iron-doped norepinephrine carbon dots according to the above ratio can allow uniform doping and a prominent reaction effect.

The norepinephrine bitartrate, the EDA, and the iron chloride are mixed in water, and based on a mass of the norepinephrine bitartrate, 20 mL to 40 mL of water are added per g of the norepinephrine bitartrate. The mixing can be assisted by ultrasound, and the reaction is conducted in a hydrothermal reactor for 8 h to 15 h. After the reaction is completed, a resulting reaction system is naturally cooled to room temperature to obtain a brown solution, the brown solution is filtered through a 0.22 μm filter membrane to remove large-particle impurities and then centrifuged at 8,000 rpm to 1,000 rpm for 10 min to 15 min, and a resulting supernatant is vacuum-dried to obtain the Fe,NA/CDs.

An embodiment of the present disclosure provides a use of the nanozyme material in the detection of a $Pb^{2+}$ ion.

Further, a method for detecting the $Pb^{2+}$ ion includes at least one selected from the group consisting of SERS and UV-Vis spectroscopy (namely, colorimetric assay). Preferably, the SERS and the UV-Vis spectroscopy may be adopted at the same time, and the results of UV-Vis spectroscopy and SERS are complementary and consistent, which improves the accuracy and reliability of detection results.

In addition, an embodiment of the present disclosure provides a method for detecting a $Pb^{2+}$ ion based on SERS, including:

mixing the nanozyme material with a $Pb^{2+}$ ion solution, adding $H_2O_2$ and a TMB solution to allow a reaction, and subjecting a resulting reaction solution to Raman spectroscopy.

TMB and $H_2O_2$ can undergo an oxidation reaction to produce blue oxTMB, and color comparison can be conducted to achieve the qualitative detection of the $Pb^{2+}$ ion. Further, SERS characteristic peaks at 872 cm⁻¹, 1,184 cm⁻¹, 1,330 cm⁻¹, and 1,607 cm⁻¹ can be observed on the SERS spectrum of oxTMB. The presence of the $Pb^{2+}$ ion will exhibit a significant inhibitory effect on the oxidation reaction, which is manifested on the SERS spectrum, that is, a peak area of the characteristic peaks decreases accordingly. Because the characteristic peak at 1,607 cm⁻¹ has a relatively large peak area, the peak area of this characteristic peak is selected to establish a linear regression equation with $Pb^{2+}$ ion concentrations in standard solutions at different concentrations. With the linear regression equation, a concentration of a $Pb^{2+}$ ion in a solution to be tested can be calculated by determining an area of a characteristic peak of the solution to be tested, thereby achieving the quantitative detection of the $Pb^{2+}$ ion.

Optionally, the nanozyme material has a concentration of 0.05 mg/mL to 0.2 mg/mL and is added at an amount of 50 µL to 100 µL. The TMB solution has a concentration of 30 mmol/L to 70 mmol/L and is added at an amount of 20 µL to 50 µL, and $H_2O_2$ has a concentration of 80 mmol/L to 150 mmol/L and is added at an amount of 20 µL to 50 µL. The SERS is conducted as follows: scanning for 10 s to 30 s with 785 nm excitation light at a laser power of 300 mW to 1,000 mW. In the above ratio ranges, the detection of $Pb^{2+}$ ions has high accuracy and sensitivity, and the detection of a $Pb^{2+}$ ion concentration range of 0.01 mg/L to 10 mg/L in a solution to be tested can be realized.

Further, an embodiment of the present disclosure provides a method for detecting a $Pb^{2+}$ ion based on UV-vis spectroscopy, including:

mixing the nanozyme material with a $Pb^{2+}$ ion solution, adding $H_2O_2$ and an ABTS solution to allow a reaction, and subjecting a resulting reaction solution to UV-vis spectroscopy.

ABTS and $H_2O_2$ can undergo an oxidation reaction to produce blue oxABTS, and color comparison can be conducted to achieve the qualitative detection of the $Pb^{2+}$ ion. Further, the characteristic absorption of oxABTS is at 415 nm on a UV absorption spectrum. The presence of the $Pb^{2+}$ ion will exhibit a significant inhibitory effect on the oxidation reaction, which is manifested on the UV absorption spectrum, that is, a corresponding absorbance value decreases accordingly. A linear regression equation is established with an absorbance value at 415 nm as an ordinate and a $Pb^{2+}$ ion concentration in each of the standard solutions at different concentrations as an abscissa. With the linear regression equation, a concentration of a $Pb^{2+}$ ion in a solution to be tested can be calculated by determining an absorbance value of the solution to be tested, thereby achieving the quantitative detection of the $Pb^{2+}$ ion.

Optionally, the nanozyme material has a concentration of 0.05 mg/mL to 0.2 mg/mL and is added at an amount of 50 µL to 100 µL. The ABTS solution has a concentration of 80 mmol/L to 130 mmol/L and is added at an amount of 20 µL to 50 µL, and $H_2O_2$ has a concentration of 80 mmol/L to 150 mmol/L and is added at an amount of 20 µL to 50 µL. In the above ratio ranges, the detection of $Pb^{2+}$ ions has high accuracy and sensitivity, and the detection of a $Pb^{2+}$ ion concentration range of 0.01 mg/L to 10 mg/L in a solution to be tested can be realized.

The features and properties of the present disclosure are further described in detail below in conjunction with examples.

Example 1

In this example, a nanozyme material (namely, Fe,NA/CDs-PB@AuNPs) was provided, and a preparation method of the nanozyme material included:

S1. 1.5 g of norepinephrine bitartrate, 0.5 g of EDA, and 0.1 g of iron chloride were weighed, dissolved in 40 mL of ultrapure water (UPW), and ultrasonically mixed thoroughly to obtain a mixed solution; the mixed solution was transferred to a polytetrafluoroethylene (PTFE)-lined hydrothermal reactor and heated at a constant temperature of 180° C. for 10 h to allow a hydrothermal reaction; after the hydrothermal reaction was completed, a resulting reaction system was naturally cooled to room temperature to obtain a brown solution; and the brown solution was filtered through a 0.22 µm filter membrane to remove large-particle impurities and then centrifuged at a high speed, and a resulting supernatant was vacuum-dried to obtain iron-doped norepinephrine carbon dots, namely, Fe,NA/CDs.

S2. 0.04 g of PB was completely dissolved in 10 mL of a 0.1 mol/L hydrochloric acid solution through stirring and then mixed with Fe,NA/CDs according to a volume ratio of 1:1, and a resulting mixture was stirred for 1 h to obtain Fe,NA/CDs-PB in which a concentration of Fe,NA/CDs was 0.1 mg/mL. A TEM image of Fe,NA/CDs-PB is shown in FIG. 1A, and it can be seen from FIG. 1A that the synthesized material is spherical and the self-assembly of PB is successful.

S3. 15 mg of Fe,NA/CDs-PB, 45 µL of 50 mmol/L $H_2O_2$, and 20 mg of sodium citrate were dissolved in 40 mL of UPW, then $HAuCl_4$ was added to obtain a mixed solution in which a concentration of $HAuCl_4$ was 10 mg/mL, and the mixed solution was stirred for 5 min to obtain Fe,NA/CDs-PB@AuNPs. A TEM image of Fe,NA/CDs-PB@AuNPs is shown in FIG. 1B, and the morphology of a core-shell structure of Fe,NA/CDs-PB@AuNPs can be seen in FIG. 1B.

Example 2

In this example, a method for detecting a $Pb^{2+}$ ion based on SERS was provided, including:

S1. 200 µL of each of $Pb^{2+}$ ion standard solutions at different concentrations (0.01 mg/mL to 1.0 mg/mL) was prepared and mixed with 50 µL of a 0.1 mg/mL Fe,NA/CDs-PB@AuNPs solution, a resulting mixture was vortexed for 30 s, and a reaction was conducted for 5 min.

S2. 50 µL of 100 mmol/L $H_2O_2$ and 20 µL of a 50 mmol/L TMB solution were added to the reaction solution obtained above, a reaction was conducted for 10 min at room temperature, and a portable Raman instrument was used to scan a resulting reaction system for 10 s with 785 nm excitation light at a laser power of 500 mW to obtain a Raman spectrum.

Figures 2A, 2B:
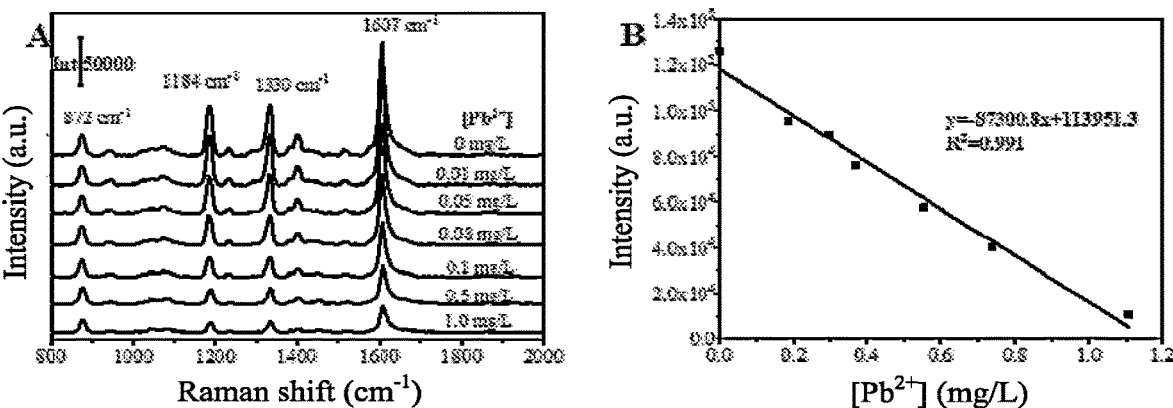
FIGS. 2A-2B show linear spectra and an equation for SERS-based detection of $Pb^{2+}$ provided in Example 2 of the present disclosure.

S3. With a peak area of a characteristic peak at 1,607 cm⁻¹ on the SERS spectrum as an ordinate and a concentration of a $Pb^{2+}$ ion standard solution as an abscissa, linear fitting was conducted to obtain the following linear regression equation (detection results were shown in FIGS. 2A-2B):

$$S = -8730.08c + 113951.33, R^2 = 0.991$$

where S represents the peak area of the characteristic peak at 1,607 $cm^{-1}$ and c represents the concentration of the $Pb^{2+}$ ion standard solution.

It can be seen that the linear regression equation has excellent correlation, and can respond well to a $Pb^{2+}$ ion solution with a concentration as low as 0.01 mg/L, indicating high sensitivity.

S4. A peak area of a characteristic peak of a solution to be tested at 1,607 $cm^{-1}$ on a SERS spectrum was determined, and a concentration of a $Pb^{2+}$ ion in the solution to be tested was calculated with the linear regression equation.

Example 3

In this example, a method for detecting a $Pb^{2+}$ ion based on UV-vis spectroscopy was provided, including:

S1. 200 μL of each of $Pb^{2+}$ ion standard solutions at different concentrations (0.01 mg/mL to 1.0 mg/mL) was prepared and mixed with 50 μL of a 0.1 mg/mL Fe,NA/CDs-PB@AuNPs solution, a resulting mixture was vortexed for 30 s, and a reaction was conducted for 5 min.

S2. 50 μL of 100 mmol/L $H_2O_2$ and 20 μL of a 100 mmol/L ABTS solution were added to the reaction solution obtained above, a reaction was conducted for 10 min at room temperature, and a UV spectrophotometer was used to acquire a UV absorption spectrum.

S3. With an absorbance value at 415 nm on the UV absorption spectrum as an ordinate and a concentration of a $Pb^{2+}$ ion standard solution as an abscissa, linear fitting was conducted to obtain the following linear regression equation (detection results were shown in FIGS. 3A-3B):

$$A = -1.09c + 1.85, R^2 = 0.992$$

where A represents the absorbance value at 415 nm and c represents the concentration of the $Pb^{2+}$ ion standard solution.

It can be seen that the linear regression equation has excellent correlation, and can respond well to a $Pb^{2+}$ ion solution with a concentration as low as 0.01 mg/L, indicating high sensitivity.

S4. An absorbance value of a solution to be tested at 415 nm was determined, and a concentration of a $Pb^{2+}$ ion in the solution to be tested was calculated with the linear regression equation.

Test Example 1

In this test example, a peroxidase-like activity of a synthesized material was determined as follows:

S1. Fe,NA/CDs, Fe,NA/CDs-PB, and Fe,NA/CDs-PB@AuNPs each were prepared into a 0.1 mg/mL solution, and 50 μL of the solution was taken as a test sample, vortexed for 30 s, and subjected to a reaction for 5 min.

S2. 50 μL of 100 mmol/L $H_2O_2$ and 20 μL of a 50 mmol/L TMB solution were added to the test sample, a reaction was conducted at room temperature for 10 min, and an absorbance value was measured at a wavelength of 652 nm to determine a peroxidase-like activity of the synthesized material.

Test results are shown in FIG. 4, and it can be seen from FIG. 4 that the test sample of Fe,NA/CDs-PB@AuNPs has the largest absorbance value at the wavelength of 652 nm and thus has the highest peroxidase-like activity.

Test Example 2

In this test example, the influence of ions coexisting with a $Pb^{2+}$ ion in a solution on the detection of the $Pb^{2+}$ ion was tested as follows:

S1. A $Pb^{2+}$ standard solution with a $Pb^{2+}$ ion concentration of 1 mg/L was prepared, $K^+$ and $Na^+$ standard solutions each with a concentration 100 times the $Pb^{2+}$ ion concentration were prepared, $Ni^{2+}$, $Mg^{2+}$, $Zn^{2+}$, $Fe^{2+}$, $Mn^{2+}$, and $Cu^{2+}$ standard solutions each with a concentration 50 times the $Pb^{2+}$ ion concentration were prepared, a $Hg^{2+}$ standard solution with a concentration 2 times the $Pb^{2+}$ ion concentration was prepared, and pure water was taken as a blank control.

S2. Each of the methods in Examples 2 and 3 was used to test each of the standard solutions prepared above, and test results were shown in FIG. 5 and FIG. 6.

Figure 5:
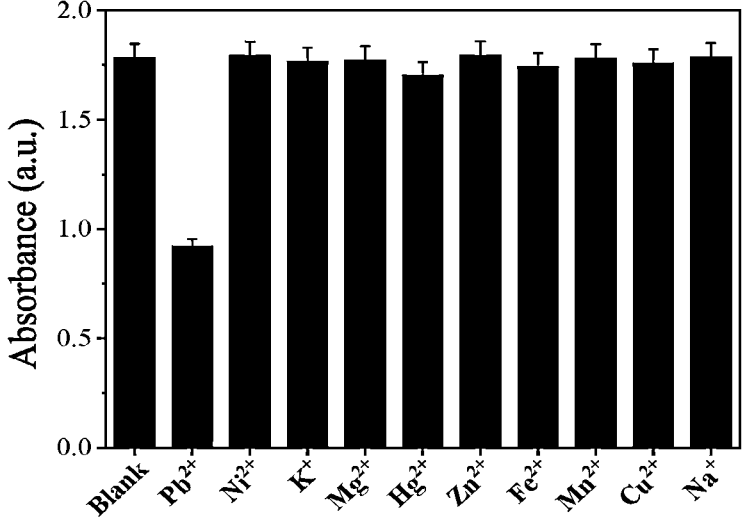
FIG. 5 shows specific test results in an ultraviolet (UV)-absorbing mode provided in Test Example 2 of the present disclosure.

It can be seen from FIG. 5 that, in a UV-absorbing mode, each ion standard solution with an ion concentration much higher than the ion concentration of the $Pb^{2+}$ standard solution still has a comparable absorbance value to the blank control, which both are about 1.5 a.u.; and an absorbance value of the $Pb^{2+}$ standard solution decreases significantly to less than 1 a.u., indicating that this detection method exhibits prominent specificity for the detection of a $Pb^{2+}$ ion.

Figure 6:
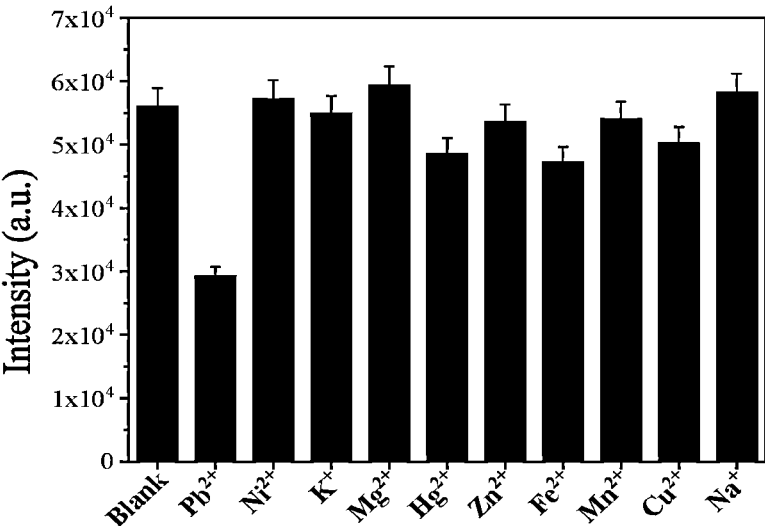
FIG. 6 shows specific test results in a SERS mode provided in Test Example 2 of the present disclosure.

Similarly, it can be seen from FIG. 6 that, in a SERS mode, each ion standard solution with an ion concentration much higher than the ion concentration of the $Pb^{2+}$ standard solution has a characteristic peak intensity value basically comparable to a characteristic peak intensity value of the blank control, which both fluctuate around $5 \times 10^4$ a.u.; and a characteristic peak intensity value of the $Pb^{2+}$ standard solution decreases significantly to less than $3 \times 10^{-4}$ a.u. In contrast, the $Hg^{2+}$ and $Fe^{2+}$ ions have weak interference with the detection of the $Pb^{2+}$ ion. However, when the SERS mode and the UV-absorbing mode are used in combination, such interference can be completely avoided. This detection method also exhibits prominent specificity for the detection of a $Pb^{2+}$ ion.

Test Example 3

In this test example, the detection methods in Examples 2 and 3 each were used to determine a $Pb^{2+}$ ion content in a tobacco leaf sample as follows:

S1. 0.5000 g of the tobacco leaf sample was weighed and placed in a 100 mL Erlenmeyer flask, 10 mL of nitric acid and 0.5 mL of perchloric acid were added, and a resulting mixture was heated on an electric hot plate for digestion; if a resulting digestion solution was tan, a small amount of nitric acid was added to digest until a white smoke was produced and a resulting digestion solution was transparent or slightly yellow; and the digestion solution was cooled, then transferred with water to a 10 mL volumetric flask, and diluted to a specified scale, and a resulting solution was thoroughly mixed for testing. A blank test was conducted according to the same method.

S2. The detection methods in Examples 2 and 3 each were used to test the solution to be tested, which both failed to detect a $Pb^{2+}$ ion concentration.

S3. A recovery rate and precision were calculated as follows:

Three $Pb^{2+}$ standard solutions at different concentrations (0 mg/kg, 5.0 mg/kg, and 10.0 mg/kg) each were added to a tobacco leaf sample. Parallel determination was conducted 3 times for each concentration. A spiked recovery rate was calculated, and a relative standard deviation (RSD) was calculated. Determination results are shown in Table 1.

TABLE 1

| | | Determined value (mg/kg) | Recovery rate (%) | RSD (%) |
|---|---|---|---|---|
| Sample | Spiked amount (mg/kg) | SERS/colorimetric assay | SERS/colorimetric assay | SERS/colorimetric assay |
| Tobacco leaf | 0 | 0 | | |
| | 5.0 | 4.76/4.71 | 95.5/94.1 | 2.5/3.7 |
| | 10.0 | 10.32/9.81 | 103.2/98.1 | 1.3/2.4 |

Tested spiked recovery rates and RSDs of tobacco leaf samples (n = 3)

It can be seen from Table 1 that a spiked recovery rate is 95.5% to 103.2% for $Pb^{2+}$ and an RSD is 1.3% to 2.5%, indicating that the detection method provided by the embodiments of the present disclosure has high accuracy and precision.

Test Example 4

In this test example, the detection methods in Examples 2 and 3 each were used to determine a $Pb^{2+}$ ion content in a rice sample as follows:

S1. A rice powder standard substance GBW(E) 100351 was selected as a sample to be tested (NCS Testing Technology Co., Ltd.); 0.3000 g of a dried rice powder sample was weighed and placed in a glass digestion tube, then 5 mL of nitric acid (super pure) was added, a cap of the tube was tightened, and soaking was conducted overnight; the tube was transferred to a reaction tank, and the tank was completely sealed; nitrogen was introduced to raise the pressure to 4,000 kPa, a temperature in an outer chamber was set to lower than 40° C., and the digestion was conducted according to a heating procedure shown in Table 2; and after the digestion was completed, the pressure was completely released, and a sample was taken out, transferred to a 10 mL volumetric flask, diluted, and thoroughly mixed for testing. A blank test was conducted.

TABLE 2

Heating procedures for rice digestion

| Step | Temperature (° C.) | Hold time/min | Power/W | Heating time/min |
|---|---|---|---|---|
| 1 | 120 | 10 | 1600 | 7 |
| 2 | 150 | 5 | 1600 | 5 |
| 3 | 180 | 15 | 1600 | 10 |

S2. The detection method in Example 2 was used to subject the solution to be tested to Raman spectroscopy at 1,607 $cm^{-1}$, and a resulting value was substituted into a linear regression equation for calculation. It was determined that a $Pb^{2+}$ concentration in the rice sample was 108.9 µg/kg and a standard value was 110±10 µg/kg. The determination results were within error ranges.

The detection method in Example 3 was used to determine the absorbance of the solution to be tested at 415 nm, and a resulting value was substituted into a linear regression equation for calculation. It was determined that a $Pb^{2+}$ concentration in the rice sample was 111.5 µg/kg and a standard value was 110±10 µg/kg. The determination results were within error ranges.

Test Example 5

In this test example, the detection methods in Examples 2 and 3 each were used to determine a $Pb^{2+}$ ion content in a vegetable sample as follows:

S1. A celery standard substance GBW10048 was selected as a sample to be tested (Institute of Geophysical and Geochemical Exploration (IGGE)); 1.000 g of a vegetable sample was accurately weighed and placed in a glass digestion tube, 5 mL of nitric acid (super pure) and 1 mL of hydrogen peroxide (super pure) were added successively, and a cap of the tube was tightened; the tube was transferred to a reaction tank, and the tank was completely sealed; nitrogen was introduced to raise the pressure to 4,000 kPa, a temperature in an outer chamber was set to lower than 40° C., and the digestion was conducted according to a heating procedure shown in Table 3; and after the digestion was completed, the pressure was completely released, and a sample was taken out, transferred to a 25 mL volumetric flask, diluted, and thoroughly mixed for testing. A blank test was conducted.

TABLE 3

Heating procedures for vegetable digestion

| Step | Temperature (° C.) | Hold time/min | Power/W | Heating time/min |
|---|---|---|---|---|
| 1 | 110 | 15 | 1500 | 5 |
| 2 | 150 | 10 | 1500 | 5 |
| 3 | 190 | 10 | 1500 | 5 |

S2. The detection method in Example 2 was used to subject the solution to be tested to Raman spectroscopy at 1,607 $cm^{-1}$, and a resulting value was substituted into a linear regression equation for calculation. It was determined that a $Pb^{2+}$ concentration in the vegetable sample was 61.9 µg/kg and a standard value was 62.3±1.9 µg/kg. The determination results were within error ranges.

The detection method in Example 3 was used to determine the absorbance of the solution to be tested at 415 nm, and a resulting value was substituted into a linear regression equation for calculation. It was determined that a $Pb^{2+}$ concentration in the vegetable sample was 63.2 µg/kg and a standard value was 62.3±1.9 µg/kg. The determination results were within error ranges.

In summary, an embodiment of the present disclosure provides a nanozyme material and a preparation method thereof. In the preparation method, PB is used to regulate a peroxidase activity of Fe,NA/CDs, and then gold nanoparticles are synthesized with Fe,NA/CDs as a reducing agent and a stabilizing agent. The nanozyme material has both a peroxidase activity and a Raman enhancement effect and can be used for nanozyme-based SERS. An embodiment of the present disclosure also provides a method for rapidly detecting a $Pb^{2+}$ ion, which is based on a color change or an additional Raman SERS signal caused by nanozyme oxidation. Such a sensing signal (colorimetric and SERS analysis) is derived from a catalytic oxidation reaction of ABTS or TMB, and the presence of $Pb^{2+}$ specifically inhibits the oxidation, such that the rapid detection of $Pb^{2+}$ can be achieved. In addition, the results of colorimetric assay and SERS are complementary and consistent, which improves the accuracy and reliability of detection results.

The above are merely preferred examples of the present disclosure and are not intended to limit the present disclosure, and various changes and modifications can be made to the present disclosure by those skilled in the art. Any modifications, equivalent substitutions, improvements, and the like made within the spirit and principle of the present disclosure should be included within the protection scope of the present disclosure.

What is claimed is:

1. A preparation method of a nanozyme material, wherein the nanozyme material is Fe, norepinephrine (NE)/CDs-Prussian blue (PB) @AuNPs, and the nanozyme material comprises iron-doped norepinephrine carbon dots Fe (NE)/CDs, a Prussian blue (PB) loaded on the iron-doped norepinephrine carbon dots Fe (NE)/CDs, and AuNPs distributed on a surface of the iron-doped norepinephrine carbon dots Fe, (NE)/CDs, and wherein the method comprises:

mixing

Fe NE/CDs-PB, $H_2O_2$, sodium citrate and $HAuCl_4$ in water to obtain a mixed solution, wherein Fe,NE/CDs-PB, $H_2O_2$, and sodium citrate are present in a mass ratio of 1:(0.02-0.2):(1-3), $H_2O_2$ is in a solution concentration of 30 mmol/L to 70 mmol/L, based on a mass of Fe,NE/CDs-PB an amount of 2 L to 4 L of water is added per g of Fe,NE/CDs-PB, and a concentration of $HAuCl_4$ in the mixed solution is 5 mg/mL to 20 mg/mL; and stirring the mixed solution at room temperature for 5 min to 10 min to obtain Fe NE/CDs-PB@AuNPs.

2. The preparation method according to claim 1, wherein a preparation method of the Fe, (NE)/CDs-PB comprises:

mixing a solution of the PB in hydrochloric acid with the Fe, (NE)/CDs to obtain the Fe, (NE)/CDs-PB.

3. The preparation method according to claim 2, wherein a mass ratio of the Fe, (NE)/CDs to the PB is 1:(20-60).

4. The preparation method according to claim 2, wherein a preparation method of the Fe (NE)/CDs comprises:

mixing norepinephrine bitartrate, ethylenediamine (EDA), and iron chloride to obtain a resulting mixture, and subjecting the resulting mixture to a second reaction at 160° C. to 200° C.

5. The preparation method according to claim 4, wherein the norepinephrine bitartrate, the EDA, and the iron chloride are in a mass ratio of 1:(0.2-0.5):(0.03-0.15).

* * * * *